United States Patent [19]

Zahniser et al.

[11] 4,395,493

[45] Jul. 26, 1983

[54] MONOLAYER DEVICE USING FILTER TECHNIQUES

[75] Inventors: David J. Zahniser, Wellesley; Gerardo L. Garcia, Harvard, both of Mass.

[73] Assignee: Coulter Electronics, Inc., Hialeah, Fla.

[21] Appl. No.: 263,712

[22] Filed: May 14, 1981

[51] Int. Cl.$^3$ .................... C12M 1/36; C12M 1/00; C12M 1/34; G01N 1/00

[52] U.S. Cl. .................................. 435/289; 356/38; 422/66; 435/287; 435/291; 435/808

[58] Field of Search .................... 356/38; 422/66, 67, 422/64; 435/284, 287, 289, 291, 803, 808

[56] References Cited

U.S. PATENT DOCUMENTS

| | | | |
|---|---|---|---|
| 3,653,773 | 4/1972 | Childs | 356/38 X |
| 3,654,091 | 4/1972 | Binnings et al. | 435/291 X |
| 3,690,832 | 9/1972 | Plakas | 435/291 X |
| 3,902,971 | 9/1975 | Fletcher et al. | 435/291 X |
| 3,940,250 | 2/1976 | Plakas et al. | 435/291 X |
| 4,084,902 | 4/1978 | Green | 356/38 |
| 4,321,122 | 3/1982 | Whitcomb et al. | 422/66 X |

FOREIGN PATENT DOCUMENTS

| | | |
|---|---|---|
| 1444759 | 8/1976 | United Kingdom . |
| 1451449 | 10/1976 | United Kingdom . |
| 1503068 | 3/1978 | United Kingdom . |
| 1571480 | 7/1980 | United Kingdom . |
| 1601316 | 10/1981 | United Kingdom . |

OTHER PUBLICATIONS

Garcia, G. L., and Tolles, W. E., "Ultrasonic Disaggregation of Cell Clusters", *J. Histochem. Cytochem.*, 25:508, 1977.

Rosenthal, D. L., Stern, E., McLatchie, C. A., Lagasse, L. D., Wall, R., and Castleman, K. R., "A Simple Method of Producing a Monolayer of Cervical Cells for Digital Image Processing", *Anal. Quant. Cytol.*, 1:84, 1979.

*Primary Examiner*—Robert J. Warden
*Attorney, Agent, or Firm*—Gerald R. Hibnick

[57] ABSTRACT

Disclosed is a monolayering device comprising a cell sensor arrangement for receiving a liquid suspension of cells and for controlling the number of cells passing through to an application vessel, a filter tape having the application vessel positioned thereabove at a first station, a vacuum source for sucking the liquid of the liquid suspension from the application vessel through the tape, a tape moving arrangement for moving the portion of the tape having the cells deposited thereon from the first station to a second station whereat a slide is positioned, and a sponge having a fixative therein mounted on a block for biasing the tape against the slide so that the cells will adhere to the slide.

9 Claims, 2 Drawing Figures

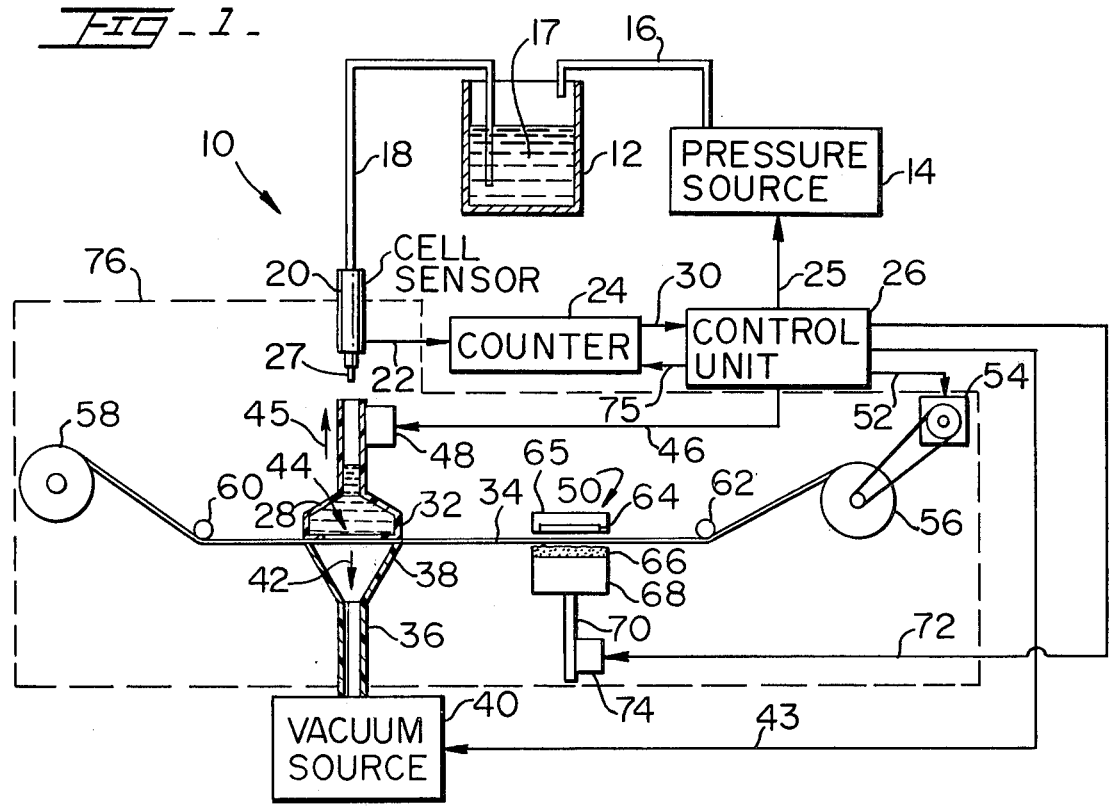
Fig-1-
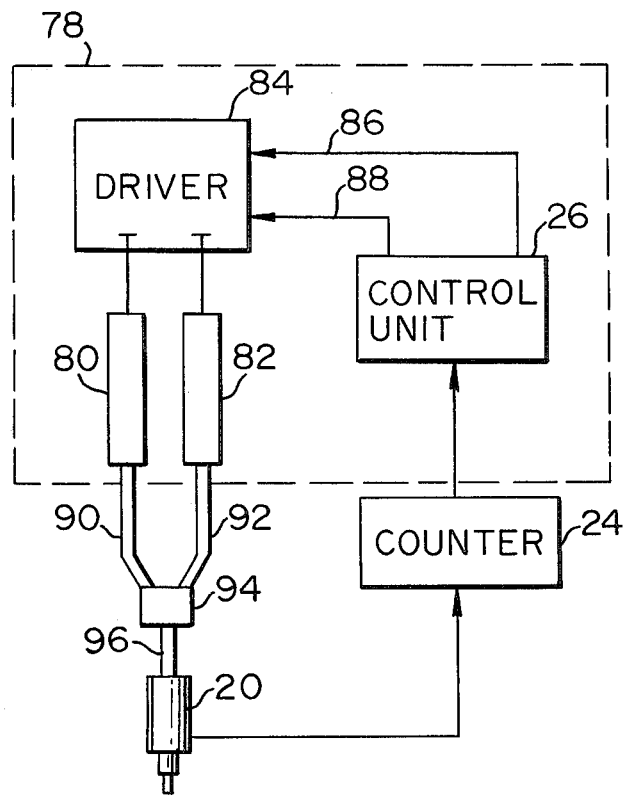
Fig-2-

MONOLAYER DEVICE USING FILTER TECHNIQUES

FIELD OF THE INVENTION

The invention generally relates to the preparation of liquid cellular specimens on microscope slides or similar substrates for subsequent examination under a microscope.

DESCRIPTION OF THE PRIOR ART

Monolayer cell preparations are usually required for automated analysis of cells and are often desirable for visual analysis as well. Monolayer preparations are typically made by collecting cells in a liquid suspension and then layering the cells onto a microscope slide. During the final placing of the cells onto the slide, care must be taken, for example, to have proper cell concentration in the liquid suspension and the correct suspension viscosity. Numerous devices are used in the prior art to spread the cells onto the slide. Such devices include spinners, wedge-making devices, or centrifugal buckets. However, the centrifugal buckets are difficult to automate, and typically spinners and wedge making devices often give unsuitable preparations.

In recent years, researchers have tried filtering the cell suspensions onto a filter and then transferring the cells from the filter to the microscope slide either by contact or by dissolving the filter as shown in the following articles: (1) Garcia, G. L., and Tolles, W. E., "Ultrasonic disaggregation of cell clusters," *J. Histochem. Cytochem.*, 25:508, 1977, and (2) Rosenthal, D. L., Stern, E., McLatchie, C., Lagasse, L. D., Wall, R., and Castleman, K. R., "A simple method of producing a monolayer of cervical cells for digital image processing," *Anal. Quant. Cytol.*, 1:84, 1979.

SUMMARY OF THE INVENTION

The present invention is directed toward a monolayering device for applying cells to a slide to be examined by a microscope or like optical device, the monolayering device comprising measuring means for obtaining a quantity of liquid suspension having a desired number of said cells therein; application vessel means at a first station for receiving the quantity of liquid and having a window formed at its bottom for applying the quantity of liquid; a filter tape capable of passing the liquid of the liquid suspension while retaining the cells; vacuum means positioned under the application vessel means and the filter tape for sucking the liquid of the liquid suspension through the tape to deposit the cells on a tape portion of the filter tape; means for moving the tape portion having the cells from the first station to a second station; means for applying a fixative to the cells to increase their adherence to the slide; and means for biasing the tape portion having the cells against the slide the cells can adhere to the slide.

BRIEF DESCRIPTION OF THE DRAWINGS

Further objects and advantages of the present invention will become apparent as the following description proceeds, taken in conjunction with the accompanying drawing in which:

FIG. 1 illustrates a generalized, schematic diagram of the monolayering device embodying the present invention.

FIG. 2 illustrates an alternative arrangement for providing the desired number of cells to the application vessel shown in FIG. 1.

DETAILED DESCRIPTION OF THE PREFERRED EMBODIMENT

A monolayering device, generally indicated by the reference numeral 10, is shown in FIG. 1 in a generalized, schematic illustration. Biological cells are processed in a conventional manner to eliminate aggregates of cells. The individually isolated cells, which are normally suspended in a suspending solution, such as an isotonic solution, are then placed in a sample bath 12. A pressure source 14 provides a positive pressure to the bath 12 by way of a conduit 16. The positive pressure applied to the bath 12 causes a sample suspension 17 containing the cells to move through a conduit 18 to a conventional cell sensor 20. The cell sensor 20 is preferably a simple particle detector capable of detecting individual particles utilizing the principle of Wallace Coulter, as described in U.S. Pat. No. 2,656,508 to Coulter. More specifically, the cell sensor is of a type wherein an electrical current is passed through a sensing zone simultaneously with the individually entrained particles so that each particle gives a particle pulse. Each particle pulse from the cell sensor 20 is fed by way of a conductor 22 to a conventional pulse detector and counter 24, such as shown in U.S. Pat. No. 2,656,508. A control unit 26 initially enables the pressure source 14 by way of a conductor 25 to start providing the positive pressure, which in turn provides the sample to the cell sensor. Also, the cell count is provided to the control unit 26 from the counter 24 by way of an electrical conductor 30. When the cell count reaches a predetermined number set in the control unit, the control unit 26 deactivates the pressure source 14, so that the flow of sample suspension to the cell sensor 29 will cease. The control unit 26 can take the form of a simple microprocessor or alternatively, hardware in the form of enabling circuitry, count threshold detection circuitry, and deactivating circuitry.

By virtue of the above described structure, a sample suspension containing a known number of cells will be provided from a nozzle 27 of the cell sensor 20 to an application vessel 28. Since the total number of cells passed to the vessel 28 remains at a preset number, the actual quantity of liquid in the sample suspension permitted to pass can vary without any adverse affect to the monolayering. Hence, the cell concentration in the suspension of the bath 12 can vary over a wide range. However, the sample suspension 17 in bath 12 must be sufficiently diluted to substantially reduce coincidence problems in counting the cells; depending upon the cellular material being processed, to allow the cells to unfold; and to wet the working area of the filter tape 34 under the window 32.

The application vessel 28 has a rectangular window 32 at its bottom which opens onto and is in contact with a filter strip or tape 34. More specifically, the tape 34 closes the window 32 and the application vessel 28 and the tape 34 rest upon a drain 36 having a top 38. The top 38 has a corresponding rectangle configuration to mate with the rectangular window 32, so as to form a water tight seal. While the sample suspension is entering the vessel 28 or after the total volume of the sample suspension enters the vessel 28, the control unit 26 enables a vacuum source 40 to provide a suction in the drain 36. This negative pressure sucks the liquid of the sample suspension through the tape 34 in the direction of arrow 42, so that the cells remain on the upper surface of the tape 34. After a predetermined time sufficient for withdrawing all liquid from the application vessel 28, the control unit 26 by way of a conductor 43 deactivates the vacuum source 40. The depositing of the cells by the application vessel 28 defines a first station or application station 44, which is the first processing stage for the tape 34.

After the cells have been deposited on the tape 34, the application vessel 28 is raised from the tape 34 in the direction of arrow 45. This is accomplished by the control unit 26 providing an enabling signal via a conductor 46 to a motorized gear assembly 48. Alternatively, the drain 36 can be lowered and the negative pressure of the vacuum source 40 maintained, so that the tape 34 is pulled downward from the vessel 28. Thereafter, the tape 34 is advanced to a second station 50. This advancement is accomplished by the control unit 26 enabling by way of a conductor 52 a motor 54 for a set length of time. The motor 54 turns a reel 56 so as to wind up the tape 34. The tape 34 is initially wound around a reel 58. Hence, the tape 34 unwinds from the reel 58, passes under a pair of rollers 60 and 62, so as to pass through the first and second stations 44 and 50, and then subsequently is wound around the reel 56.

As previously mentioned, the portion of the tape 34 having the cells deposited thereon is advanced from the first station 44 to the second station 50. At the second station 50, a slide 64 is mounted by a slide holder 65 in adjacent, spaced-apart relationship to the tape 34. A hard sponge 66 is mounted on top of a block 68 having an extension portion 70. After the tape 34 has been advanced, the control unit 26 by way of a conductor 72 will enable a motorized gear assembly 74 to press the hard sponge 66 against the tape 34, thereby pressing the tape 34 against the slide 64. Prior to this step a fixative was spread over the sponge 66. Hence, the fixative is in turn applied to the cells, which not only fixes the cells, but helps them to adhere to the slide 64. One known illustrative fixative that can be used in the present invention contains in one liter: 95% ethanol (107.7 milliters); distilled water (995.2 milliters); sodium chloride (7.7 grams) and thymol (0.25 grams). As soon as the sponge 66 is moved forward, the gear assembly 74 is reversed in direction by the control unit 26, so that the tape 34 and the sponge 66 are removed from the slide 64. Thereafter, the slide is manually removed. However, automated means of positioning the slide and thereafter removing the slides can be implemented by known devices in the art. Hence, at this second station 50, the cells are transferred from the tape 34 to the slide 64 where the fixative allows the cells to stick to the slide 64.

After the transfer of the cells to the slide, the above process can now be repeated. The control unit 26, by reversing the motorized gear assembly 48, moves the vessel 28 back into contact with a new portion of the tape 34. The control unit 26 resets the counter 24 to zero by way of an electrical conductor 75. The control unit 26 then activates the pressure source 14 to begin the entire process over again.

Each of the above steps which are accomplished by the control unit 26 can likewise be manually accomplished by an operator; thereby eliminating the need for a control unit 26. The supports for the elements of FIG. 1 is generally shown by a support means 76, which can take many different forms and can in fact be a plurality of supports, brackets and stands, but for the sake of simplicity, will be described as a single support structure. The reels 56 and 58 are rotatably supported to the support means 76. The motorized gear assemblies 48 and 74, which are alternatively reversed in direction, are rigidly fixed to the support means 76, so as to allow the vessel 28 and the block 68, respectively, to move up and down with respect to support means 76. The cell sensor 20, the drain 36, the motor 54, and the slide holder 65 are rigidly attached to the support means 76. If desirable, the slide holder means 65 can be adapted to an automated device for moving different slides into place.

FIG. 2 illustrates an alternative arrangement for depositing a given number of cells in the application vessel 28. Unlike the first arrangement of FIG. 1 wherein the total number of particles are counted, in this arrangement the rate at which the cells are deposited in the vessel 28 is determined and adjusted to a desired rate that will give the proper number of cells after a given time period of fluid flow through the cell sensor 20. This arrangement uses a commercially available microprocessor, such as the iSBC 86/12A, manufactured by Intel Corporation of Santa Clara, Calif., to control a syringe driving unit 78. Included with the unit 78 is a pair of syringes 80 and 82. The syringe 80 contains the sample and the syringe 82 contains a diluent, such as an isotonic saline solution. A driving means 84 causes positive displacement of the syringes 80 and 82 individually, so as to provide a desired ratio between the liquid flows from the two syringes. The rate of flows from the two syringes 80 and 82, and therefore the ratio of two flows, is set by the control unit 26 via conductors 86 and 88, respectively. In this arrangement, the control unit 26 is a microprocessor, and can also serve the enabling and deactivating functions that the control unit 26 provided in the first embodiment. Hence, the same connection between the control unit 26 and various components of the system that are shown in FIG. 1 would be also implemented with this arrangement, but are not shown in FIG. 2. In operation, the control unit 26 would monitor the counts provided by the pulse detector and counter 24 to determine the rate at which particle pulses are counted. The control unit 26 is programmed to have in memory a desired counting rate, which is compared to the actual counting rate. If the actual counting rate deviates from the desired counting rate, the relative flow rates from the syringes 80 and 82 are correspondingly adjusted. The flows from the syringes 80 and 82 pass through a pair of conduits 90 and 92, respectively, so as to be mixed in a mixing junction 94. Thereafter, the mixture is fed through a conduit 96 to the sensor 20. The remainder of the device 10 is as shown in FIG. 1. With the monitored flow through the cell sensor 20 having the desired counting rate, the control unit 26 will stop the forward driving action of the driver means 84 at a predetermined time. This predetermined time is set so that with the desired count rate, the proper number of cells will be contained within the application vessel 28 at the end of each operational cycle.

Slide specimens prepared in the above described manner show a high rate of transfer of cells to the slide 64 and very good adherence to it. Moreover, the monolayering device 10 is easy to clean, and the use of the filter tape 34 both helps to relieve the problem of contamination, as well as to simplify the multi-station design. The use of the device can be for many different purposes, a few illustrative applications would be for cervical-cell samples, urine samples, and sputum samples. Moreover, it is contemplated that the device 10 can be used for body fluids as well as disaggregated tissue fragments or tissue culture samples.

Although particular embodiments of the invention have been shown and described herein, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A monolayering device for applying cells from a liquid suspension to a slide to be examined, comprising: measuring means for obtaining a quantity of the liquid suspension having therein a desired number of said cells; application vessel means located at a first station for receiving said quantity of liquid; a filter tape for receiving at said first station the liquid suspension from said application vessel means, said filter tape being capable of passing the liquid of the liquid suspension, while retaining said cells; vacuum means coupled to said application vessel means for sucking the liquid of the liquid suspension through said tape, thereby to deposit the cells on a tape portion of said filter tape; moving means for moving said tape portion having said cells from said first station to a second station; and biasing means for biasing said tape portion having the cells against the slide at said second station and thereby causing the cells to adhere to the slide.

2. The monolayering device according to claim 1, wherein said application vessel means has a window facing said filter tape through which the liquid suspension is fed onto said tape portion.

3. The monolayering device according to claim 1, wherein said biasing means comprises a sponge movably mounted to engage said tape so as to force said tape against the slide.

4. The monolayering device according to any one of claims 1, 2 or 3, wherein said biasing means has fixative supplied thereto, whereby fixative is applied to said cells when said biasing means engages said tape.

5. The monolayering device according to claim 1, wherein said measuring means comprises a cell counter.

6. The monolayering device according to claim 5, wherein said measuring means includes moving means for moving said liquid suspension in a liquid flow, and stopping means for stopping said liquid flow after said cell counter has detected a predetermined number of cells.

7. The monolayering device according to any one of claims 1, 3, or 5, wherein said measuring means is constructed and arranged for providing a flow of said suspension liquid for a predetermined time period at preferred flow rate.

8. The monolayering device according to claims 5 or 6, including flow rate control means which monitors the count rate by said cell counter and then adjusts the flow rate of the liquid suspension so that the counting rate achieves a predetermined value.

9. The monolayering device according to any one of claims 1, 3 or 6, in which said measuring means includes mixing means for mixing a diluent with the liquid suspension and control means for varying the amount of the liquid suspension relative to the amount of the diluent.

* * * * *